United States Patent [19]
Challener

[11] Patent Number: 5,986,762
[45] Date of Patent: Nov. 16, 1999

[54] OPTICAL SENSOR HAVING OPTIMIZED SURFACE PROFILE

[75] Inventor: William A. Challener, Grant, Minn.

[73] Assignee: Imation Corp., Oakdale, Minn.

[21] Appl. No.: 09/094,890

[22] Filed: Jun. 15, 1998

[51] Int. Cl.$^6$ .................................................. G01B 11/24
[52] U.S. Cl. .......................................... 356/375; 356/403
[58] Field of Search .................................... 356/317, 328, 356/375, 318, 345, 403, 237.2, 237.3; 436/164

[56] References Cited

U.S. PATENT DOCUMENTS

| | | |
|---|---|---|
| 4,828,387 | 5/1989 | Sawyers et al. .......................... 356/319 |
| 4,877,747 | 10/1989 | Stewart . |
| 4,882,288 | 11/1989 | North et al. . |
| 4,931,384 | 6/1990 | Layton et al. . |
| 4,992,385 | 2/1991 | Godfrey . |
| 5,035,863 | 7/1991 | Finlan et al. . |
| 5,071,248 | 12/1991 | Tiefenthaler . |
| 5,118,608 | 6/1992 | Layton et al. . |
| 5,310,686 | 5/1994 | Sawyers et al. . |
| 5,322,798 | 6/1994 | Sadowski ................................ 356/345 |
| 5,442,448 | 8/1995 | Knoll . |
| 5,455,178 | 10/1995 | Fattinger .................................. 385/30 |
| 5,478,755 | 12/1995 | Attridge et al. . |
| 5,492,840 | 2/1996 | Malmqvist et al. . |
| 5,583,643 | 12/1996 | Gass et al. . |
| 5,598,267 | 1/1997 | Sambles et al. . |
| 5,636,633 | 6/1997 | Messerschmidt et al. . |
| 5,751,482 | 5/1998 | Challener, IV . |
| 5,776,785 | 7/1998 | Lin et al. . |

FOREIGN PATENT DOCUMENTS 0 321 523  2/1992  European Pat. Off. .

OTHER PUBLICATIONS

"Unusual splitting behavior of the dispersion of surface polaritons in grating of different symmetry, amplitude, and profile", *Applied Optics*, B. Fischer, vol. 34, No. 25, Sep. 1, 1995, pp. 5773–5779.

"A Compact Surface Plasmon Resonance Sensor for Measurement of Water in Process", *Applied Spectroscopy*, R. Matsubara, vol. 42, No. 8, 1988, pp. 1375–1379.

"Detection of Immuno–complex Formation via Surface Plasmon Resonance on Gold–Coated Difraction Gratings", *Biosensors*, 3, 1987/88, D. C. Cullen, pp. 211–225.

"Grating–Coupled Surface Plasmon for Measuring the Refractive Index of a Liquid Sample", *J. Phys. D: Applied Physics*, Hiroshi Kano, vol. 34, 1995, pp. 331–335.

"Polarisation Conversion Through the Excitation of Surface Plasmons on a Metallic Grating", *Journal of Modern Optics*, G. P. Bryan–Brown, 1990, vol. 37, No. 7, pp. 1227–1232.

(List continued on next page.)

*Primary Examiner*—Frank G. Font
*Assistant Examiner*—Tu Nguyen
*Attorney, Agent, or Firm*—Eric D. Levinson

[57] ABSTRACT

A method and apparatus for optically assaying a targeted substance in a sample using a sensor having an optimized groove profile. The optical sensor has a grooved surface defined by a first sinusoidal component superposed with one or more additional sinusoidal components such that a reflectance anomaly occurs at multiple resonance angles. A measure of the targeted substance in the sample can more precisely calculated as a function of a change in angular distance between the resonance angles. Advantages of the present invention include increased sensitivity and less susceptibility to system drifts due to mechanical motion and thermal changes than conventional diffraction grating sensors.

41 Claims, 7 Drawing Sheets

OTHER PUBLICATIONS

"Resonance Anomalies in the Light Intensity Reflected at Silver Gratings with Dielectric Coatings", *J. Phys. D: Applied Physics*, I. Pockrand, vol. 9, 1976, pp. 2423–2432.

"Surface–Resonance Polarization Conversion Mediated By Broken Surface Symmetry", *The American Physical Society, Physical Review B*, S. J. Elston, vol. 44, No. 7, Aug. 15, 1991–I, pp. 3483–3485.

"Gas Detection By Means of Surface Plasmon Resonance", *Sensors and Actuators*, Claes Nylander, vol. 3, 1982–83, pp. 79–88.

"A Direct Surface Plasmon—Polariton Immunosensor: Preliminary Investigation of the Non–specific Adsorption of Serum Components to the Sensor Interface", *Sensors and Actuators*, D. C. Cullen, B1, 1990, pp. 576–579.

"Surface Plasmon Resonance on Gratings as a Novel Means for Gas Sensing", *Sensor and Actuators*, P. S. Vukusic, B, 8, 1992, pp. 155–160.

"Development of a Prototype Gas Sensor Using Surface Plasmon Resonance on Gratings", *Sensors and Actuators*, M. J. Jory, B, 17, 1994, pp. 203–209.

"Double Excitation of a Resonant Surface Plasmon Maximum", *Journal of Modern Optics*, M.J. Jory, 1993, vol. 40, No. 9, pp. 1657–1662.

"Optimization of a Chemooptical Surface Plasmon Resonance Based Sensor", *Applied Optics*, Jos van Gent, vol. 29, No. 19, Jul. 1, 1990, pp. 2843–2849.

"Choice of Metal and Wavelength for Surface–Plasmon Resonance Sensors: Some Considerations", *Applied Optics*, Helene E. de Bruijn, vol. 31, No. 4, Feb. 1992.

"Detection of Amine Gases by Color Changes of Acid–Base Indicators Supported on Inorganic Films", *Reports of the Faculty of Engineering Nagasaki University*, Yuji Takao, vol. 26, No. 46, Jan. 1996, pp. 105–111.

"Properties and Applications of Layered Grating Resonances", SPIE, *Application and Theory of Periodic Structures, Diffraction Gratings, and More Phenomena III*, G. Gallatin, vol. 815, 1987, pp. 158–167.

"Vector Diffraction of a Grating with Conformal Thin Films", *Optical Society of America*, W. A. Challener, vol. 13, No. 9, Sep. 1996, pp. 1859–1869.

*Handbook of Biosensors and Electronic Noses: Medicine, Food and the Environment*, Chapters 7, 16 & 24–27.

*Indicators*, Chapter 1, History of Indictors.

OPTICAL SENSOR HAVING OPTIMIZED SURFACE PROFILE

FIELD OF THE INVENTION

This invention relates generally to the field of optical assaying, and more particularly to an optical sensor having a grooved surface that is optimized to increase sensitivity and reduce susceptibility to false measurements.

BACKGROUND OF THE INVENTION

Extremely sensitive optical sensors have been constructed by exploiting an effect known as surface plasmon resonance (SPR). These sensors are capable of detecting the presence of a wide variety of materials in concentrations as low as picomoles per liter. SPR sensors have been constructed to detect many biomolecules including keyhole limpet hemocyanin, α-fetoprotein, IgE, IgG, bovine and human serum albumin, glucose, urea, avidin, lectin, DNA, RNA, HIV antibodies, human transferrin, and chymotrypsinogen. Additionally, SPR sensors have been built which detect chemicals such as polyazulene and nitrobenzenes and various gases such as halothane, trichloroethane and carbon tetrachloride.

An SPR sensor is constructed by sensitizing a surface of a substrate to a specific substance. Typically, the surface of the substrate is coated with a thin film of metal such as silver, gold or aluminum. Next, a monomolecular layer of sensitizing material, such as complementary antigens, is covalently bonded to the surface of the thin film. In this manner, the thin film is capable of interacting with a predetermined chemical, biochemical or biological substance. When an SPR sensor is exposed to a sample that includes a targeted substance, the substance attaches to the sensitizing material and changes the effective index of refraction at the surface of the sensor. Detection of the targeted substance is accomplished by observing the optical properties of the surface of the SPR sensor.

The most common SPR sensor involves exposing the surface of the sensor to a light beam through a glass prism. At a specific angle of incidence, known as the resonance angle, a component of the light beam's wavevector in the plane of the sensor surface matches a wavevector of a surface plasmon in the thin film. At this angle of incidence a very efficient energy transfer and excitation of the surface plasmon occurs in the thin film. As a result, the amount of reflected light from the surface of the sensor changes. Typically, the reflected light exhibits an anomaly, such as a sharp attenuation or amplification, and the resonance angle of an SPR sensor can be readily detected. When the targeted substance attaches to the surface of the sensor, a shift in the resonance angle occurs due to the change in the refractive index at the surface of the sensor. A quantitative measure of the concentration of the targeted substance can be calculated according to the magnitude of shift in the resonance angle.

SPR sensors have also been constructed using metallized diffraction gratings instead of prisms. For SPR grating sensors, resonance occurs when a component of the incident light polarization is perpendicular to the groove direction of the grating and the angle of incidence is appropriate for energy transfer and excitation of the thin metal film. As with prism-based sensors, a change in the amount of light reflected is observed when the angle of incidence equals the resonance angle. Previous SPR grating sensors have incorporated square-wave or sinusoidal groove profiles.

Another highly-sensitive sensor that has been recently developed is known as a "diffraction anomaly" sensor. Diffraction anomaly sensors include a substrate and a thin metal layer that are substantially the same as in an SPR grating sensor. In a diffraction anomaly sensor, however, a dielectric layer is formed outwardly from the metal layer and protects the metal layer from oxidation and general degradation. Typically, a sensitizing layer is formed outwardly from the dielectric layer. Diffraction anomaly sensors, like SPR sensors, exhibit a change in reflectivity, referred to as a diffraction anomaly, when exposed with a light beam at a particular angle of incidence. Unlike conventional SPR sensors, diffraction anomaly sensors exhibit a change in reflectivity for light polarized parallel to the grooves of the substrate. When a light beam has an angle of incidence equal to the diffraction anomaly angle for the sensor, the diffracted light beam propagates within the dielectric layer. In this manner, the dielectric layer acts as a waveguide and the controller readily detects a change in reflectivity. The thickness of the dielectric layer directly affects the diffraction anomaly. The effective index of refraction at the surface of the diffraction anomaly sensor changes in a manner similar to an SPR sensor when the diffraction anomaly sensor is exposed to a sample containing the targeted substance. Furthermore, the change in the diffraction anomaly angle is strongly dependent upon the amount of targeted substance present in the sample. In this manner, the diffraction anomaly sensor exhibits a shift in the anomaly angle that is comparable to an SPR sensor, even though the metal grating of the diffraction anomaly sensor is coated with a dielectric layer. Therefore, a quantitative measure of the targeted substance can be calculated by measuring the resulting shift in the anomaly angle.

In addition to individual sensors, there is considerable commercial interest in multiple-sensor systems that are capable of detecting a variety of targeted substances, such as certain odors, vapors, gases and other chemical species, in a surrounding environment or sample. By utilizing several sensors, such sensing systems are capable of simultaneously detecting several targeted substances. Other multiple-sensor systems utilize multiple sensors to recognize the presence of a single targeted substance. In this configuration, the burden of recognition does not lie upon a single sensor, but rests on the sensing system's ability to properly interpret and recognize output patterns of the multiple sensors. Due to the use of multiple sensors, conventional multiple-sensor sensing systems are typically extremely expensive. Furthermore, conventional sensing systems are inherently complicated and therefore are not very portable.

Current optical sensing systems that incorporate SPR sensors or diffraction anomaly sensors must precisely measure an absolute shift in the resonance angle in order to accurately calculate substance concentration. One inherent deficiency with this technique is that slight mechanical changes in the sensor affect the angle of incidence, thereby leading to false resonance shifts. Additionally, any slight deviation in the wavelength of the incident light may cause a shift in resonance angle and lead to faulty results. For the reasons stated above, and for other reasons stated below which will become apparent to those skilled in the art upon understanding the present invention, there is a need in the art for an optical sensor having improved sensitivity and less susceptibility to system variations.

SUMMARY OF THE INVENTION

As explained in detail below, the present invention is directed to a method and apparatus for optically assaying a targeted substance in a sample using a sensor having an optimized groove profile. The optical sensor has a grooved surface having a cross-sectional profile that has a first sinusoidal component superposed with one or more additional sinusoidal components such that a reflectance anomaly occurs at multiple resonance angles. A measure of the targeted substance in the sample can be calculated more precisely than with conventional optical sensors and is determined by measuring any relative change in angular distance between resonance angles. Preferably, the cross-sectional profile has a first sinusoidal component corresponding to a first harmonic of the profile and a second sinusoidal component corresponding to a third harmonic of the profile such that the resonance angles shift apart as the sensor contacts targeted substances.

In one embodiment, the present invention is an SPR sensor having a metal layer formed outwardly from the surface of the substrate and a sensitizing layer formed outwardly from the metal layer for interacting with the substance in the sample. In another embodiment, the present invention is a diffraction anomaly sensor having a metal layer formed outwardly from the surface of the substrate and a dielectric layer formed outwardly from the metal layer. According to one aspect, the sensors are formed as sensor disks.

According to another aspect, the present invention is a sensing system that includes a sensor having a substrate with a grooved surface. A cross-sectional profile of the surface has a first sinusoidal harmonic (such as the first fundamental harmonic) and a second sinusoidal harmonic (such as the third fundamental harmonic) such that a reflectance anomaly occurs at a first resonance angle and a second resonance angle. The sensing system further includes a light source for exposing the sensor with a light beam and a detector for receiving light reflected from the sensor and producing an output signal representative of an intensity of the reflected light. A controller coupled to the detector calculates a measure of the substance in the sample as a function of the output signal.

According to yet another aspect, the present invention is a method for assaying a substance in a sample. A sensor having a substrate with a grooved surface is provided, wherein a cross-sectional profile of a surface of the sensor has a first sinusoidal component and a second sinusoidal component such that a reflectance anomaly occurs at a first resonance angle and a second resonance angle. The sensor is exposed with a light beam over a range of incidence angles and interacted with the sample. A measure of the substance in the sample is determined as a function of a change in angular distance between the first and second resonance angles.

These and other features and advantages of the invention will become apparent from the following description of the preferred embodiments of the invention.

DETAILED DESCRIPTION

In the following detailed description, references are made to the accompanying drawings that illustrate specific embodiments in which the invention may be practiced. Electrical, mechanical and structural changes may be made to the embodiments without departing from the spirit and scope of the present invention. The following detailed description is, therefore, not to be taken in a limiting sense and the scope of the present invention is defined by the appended claims and their equivalents.

Figure 1:
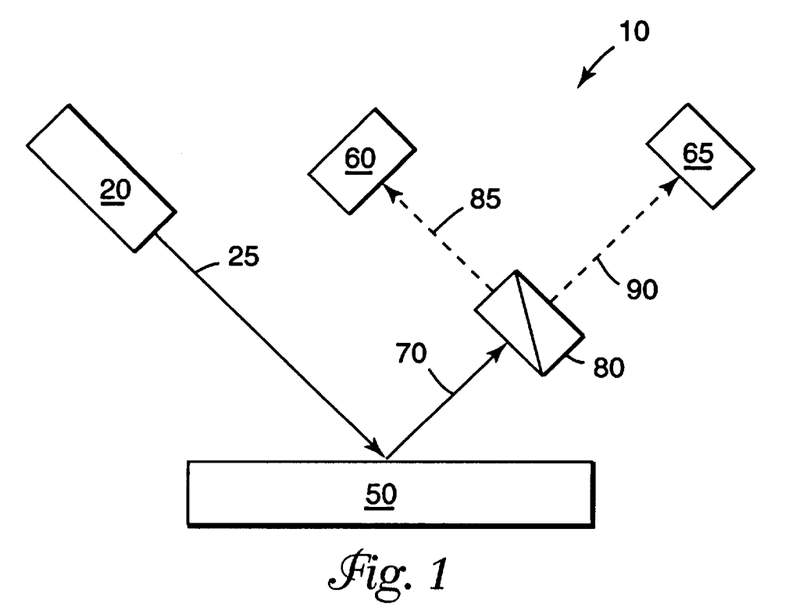
FIG. 1 is a schematic side view of one embodiment of a sensing system incorporating the optical sensor of the present invention.

FIG. 1 illustrates one embodiment of a sensing system 10 having a sensor 50 in accordance with the present invention. Sensing system 10 includes light source 20, sensor 50, detector 60, detector 65 and polarizing beamsplitter 80. Light source 20, such as a laser, produces a light beam 25 incident upon sensor 50. Sensor 50 reflects light beam 25 as light beam 70 onto polarizing beamsplitter 80. Polarizing beamsplitter 80 splits light beam 70 into component 85 and component 90 which are incident upon detector array 60 and detector array 65, respectively.

In one embodiment, sensor 50 is a surface plasmon resonance (SPR) sensor having a metallized diffraction grating that is sensitized for interaction with a targeted substance. In another embodiment, sensor 50 is a diffraction anomaly sensor having a metal grating that is coated with a dielectric layer as discussed in detail below. Conventional SPR sensors and diffraction anomaly sensors exhibit a change in reflectivity when exposed with light beam 25 at a particular angle of incidence known as a resonance angle. For SPR sensors, the change in reflectivity occurs for light polarized parallel to the grating grooves rather than perpendicular to the grating grooves. For diffraction anomaly sensors, the change in reflectivity occurs for light polarized parallel to the grating grooves rather than perpendicular to the grating grooves. As described in detail below, sensor 50 may be designed in accordance with the present invention to exhibit a change in reflectivity at two or more resonance angles. When sensor 50 is smeared with a sample containing a targeted substance, the effective index of refraction at the surface of sensor 50 changes. This change in the index of refraction in turn shifts the resonance angles at which the reflective anomaly occurs. The magnitude of the shift is strongly dependent upon the amount of targeted substance present in the sample. A quantitative measure of the targeted substance can be calculated by measuring the relative change in angular distance between the resonance angles. This is highly advantageous since conventional sensors require measurement of an absolute shift in a single resonance angle. By measuring the angular separation between two anomaly angles, the sensitivity of sensing system 10 and sensor 50 is at least twice that of conventional SPR sensors.

Another advantage of measuring relative angular separation of multiple resonance angles is that sensing system 10 is less susceptible to system drifts due to mechanical motion and thermal changes than are conventional SPR sensors. Since conventional systems depend upon precise measurement of an absolute angle, any mechanical drift in the angle of incidence can result in faulty readings. By measuring the change in angular distance between resonance angles, sensing system 10 substantially reduces the effect of mechanical drifts. Furthermore, another advantage of sensor 50 is that it may be designed such that the magnitude of the change in reflectivity is approximately equal at each resonance angle, thereby facilitating accurate measurement and reducing chances for error.

After exposing sensor 50 to the sample, the new anomaly angles for sensor 50 are determined by directing light beam 25 to sensor 50 over a range of incidence angles. In one embodiment, sensor 50 is pivoted so as to vary the angle of incidence of light beam 25. In another embodiment, sensor 50 is fixed and light source 20 is translated so as to direct light beam 25 to sensor 50 over a range of incidence angles. Polarizing beamsplitter 80 splits light beam 70 such that component 85 is polarized parallel to the grooves of the surface of sensor 50 and component 90 is polarized perpendicular to the grooves of the surface of sensor 50. A controller (not shown) monitors detectors 60 and 65 and continuously ratios the intensities of light component 85 and light component 90 received by detectors 60 and 65. In this manner, light fluctuations of the light source, or other system variations such as ripples in the sample, do not affect the calculation of the targeted species in the sample. Based on the calculated ratio for each sensing element for detectors 60 and 65, the controller determines new resonance angles and calculates a measure of the targeted substance in the sample based on a change in the angular distance between resonance angles. In one embodiment, the controller sounds an alarm when the calculated measure of the targeted substance exceeds a predetermined threshold. After sensing is complete, SPR grating sensor 50 may be disposed or may be washed and reused.

Figure 2:
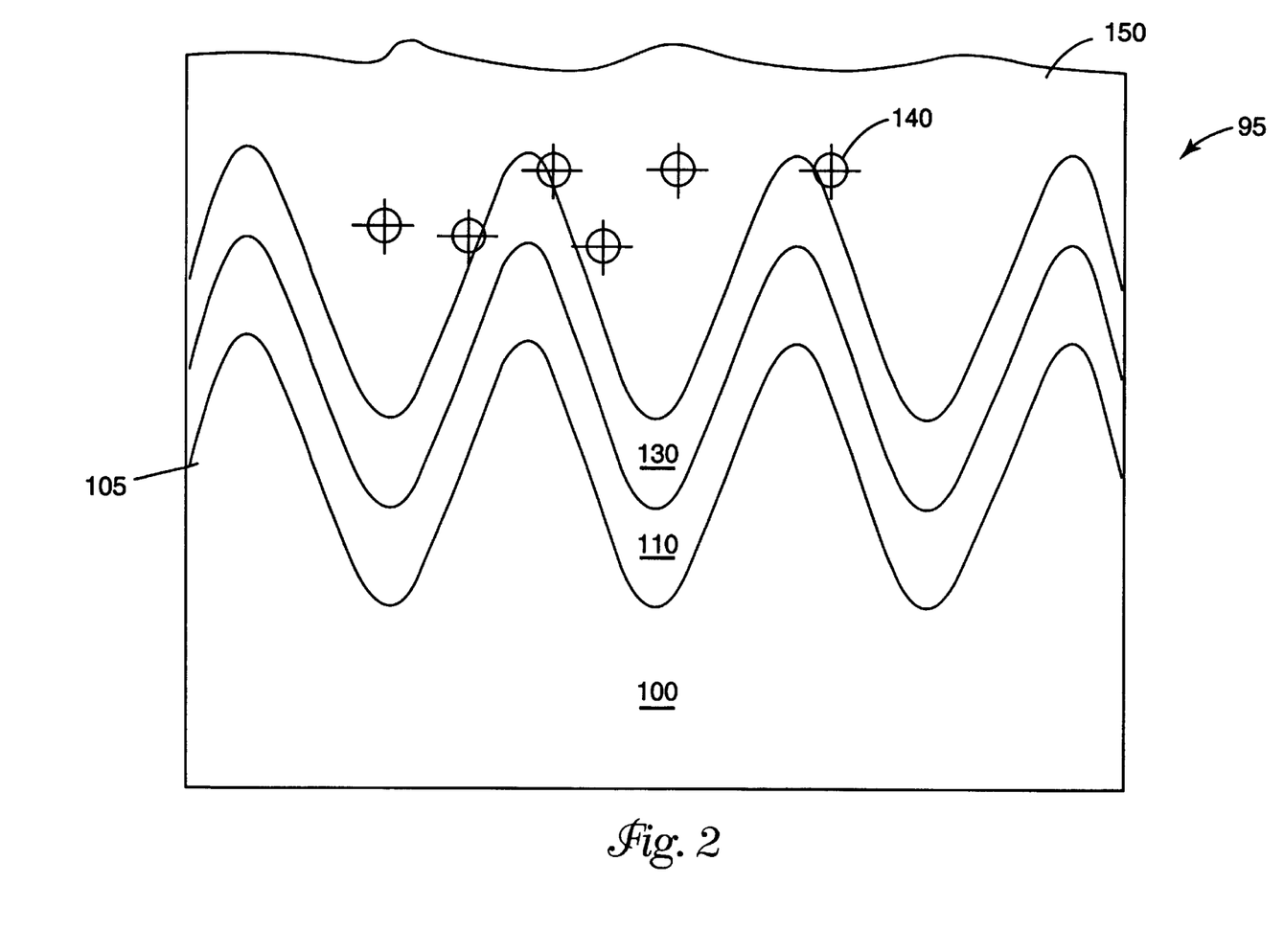
FIG. 2 is a cross-sectional view of one embodiment of an optical sensor having a groove profile with a single sinusoidal component.

FIG. 2 is a cross-sectional profile of a conventional SPR sensor 95 having surface 105 with sinusoidal grooves. The period of the groove profile of surface 105 may range from less than 0.4 micrometers to over 2.0 micrometers. Thin metal layer 110 is formed outwardly from surface 105 of substrate 100 and comprises any suitable metal such as aluminum, gold or silver. In one embodiment, layer 110 comprises silver having a thickness of approximately 100 nm. Sensitizing layer 130 is formed outwardly from layer 110. Sensitizing layer 130 is selected to interact with a predetermined chemical, biochemical or biological substance 140 contained in sample 150. In one embodiment, sensitizing layer 130 comprises a layer of antigens capable of trapping a complementary antibody. Recently, several techniques have been developed for attaching antigens as a receptive material to layer 110 such as spin coating with a porous silica sol-gel or a hydrogel matrix. Preferably, sensitizing layer 130 is less than 100 nm thick.

The following general equation can be used for determining resonance angles of conventional grating-based SPR sensors for various integers m:

$$\sin\theta_{SP} = -\left(\frac{m\lambda}{n_0 p}\right)\cos\phi_{SP} \pm \sqrt{\left(\frac{n_m^2 - K_m^2}{n_0^2 + n_m^2 - K_m^2}\right) - \left(\frac{m\lambda}{n_0 p}\sin\phi_{SP}\right)^2}$$

In this equation, $\phi_{SP}$ is the azimuthal angle of the incident light with respect to the grooves of surface 105, where 0° corresponds to the plane of incidence perpendicular to the groove direction, $n_O$ is the index of refraction of sample 150, $n_m + iK_m$ is the index of refraction for metal layer 110, $\lambda$ is the wavelength of light beam 25, and p is the period of the grooves of surface 105. When the plane of incidence of the light is perpendicular to the grooves of surface 105, i.e. $\phi_{SP}$ equals 0°, the general equation can be simplified to the following equation for calculating a resonance angle for each integer m:

$$\sin\theta_{SP} = +-\sqrt{\frac{n_m^2 - K_m^2}{n_0^2 + n_m^2 - K_m^2}} + -\frac{m\lambda}{n_0 p}$$

Furthermore, when the surface follows a single sinusoidal profile a dominant resonance will occur for m equal to 1.

In accordance with the present invention, it is observed that an SPR sensor may be constructed to exhibit a change in reflectivity at multiple resonance angles by forming a grooved substrate where the cross-sectional groove profile has multiple sinusoidal components. Each sinusoidal component of the groove profile has a corresponding resonance angle. If, for example, the grooved surface follows a single sinusoidal profile of period p, a single dominant resonance angle for m=1 will be observed. If, however, the surface profile has a sinusoidal component of period p superposed with another sinusoidal component of period p/2, an additional resonance angle will be observed for m=2. Similarly, if the surface is defined by a sinusoidal component of period p superposed with a sinusoidal component of period p/3, the m=1 and m=3 resonance angles will be observed. This embodiment is particularly useful because the resonance angles shift in opposite directions as the index of refraction at the surface of the SPR sensor changes due to contact with a targeted substance. Adjusting the amplitude (peak-to-peak depth) of the sinusoidal components controls the magnitude of the reflective anomaly at each resonance angle. Preferably, the SPR sensor is constructed such that at least two resonance angles that exhibit a change in reflectivity of at least 20%.

Figure 3:
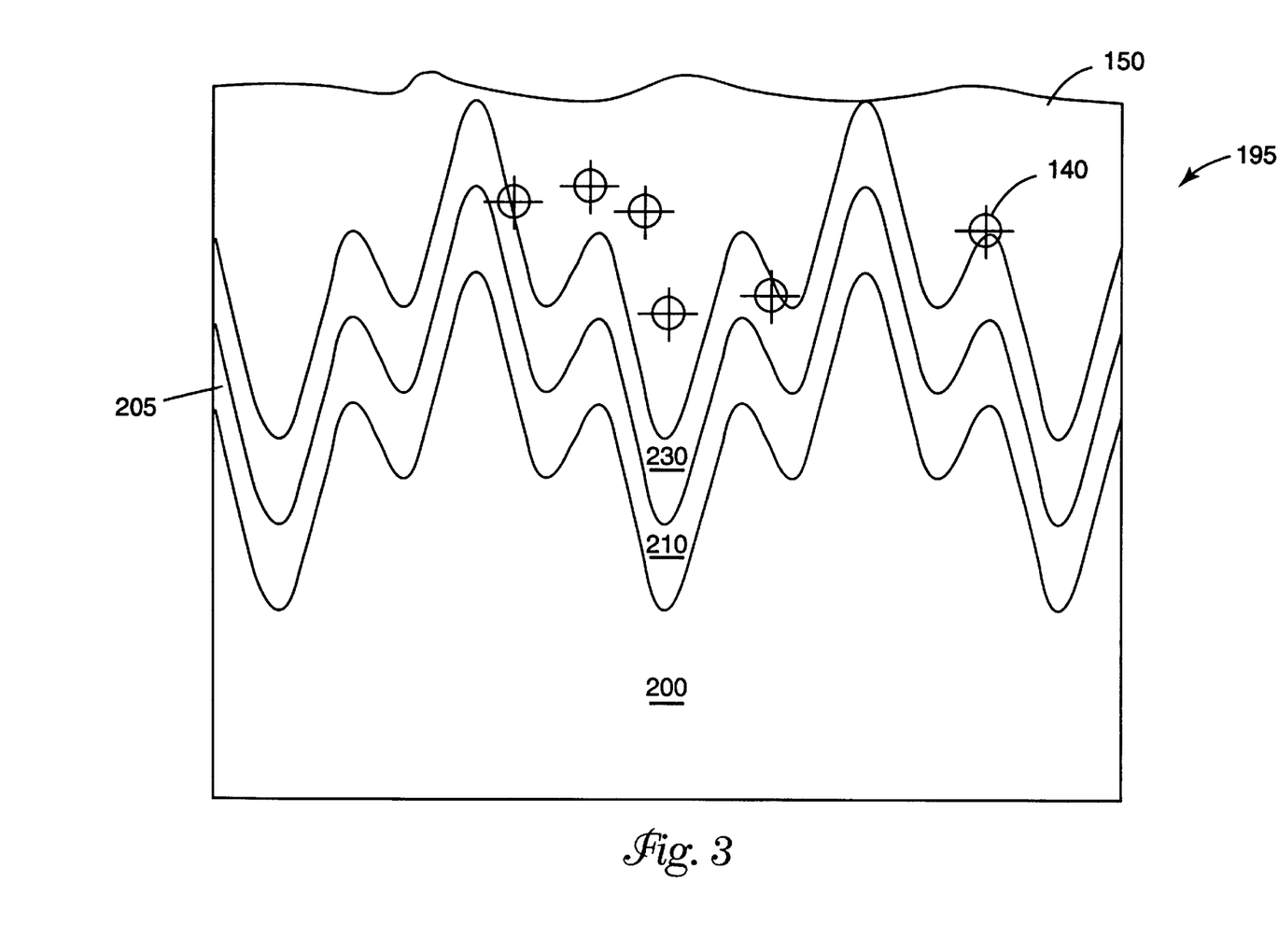
FIG. 3 is a cross-sectional view of one embodiment of an optical sensor having a groove profile with multiple sinusoidal components in accordance with the present invention.

FIG. 3 is a cross-sectional view of one embodiment of an SPR sensor 195 having a surface profile according to the present invention. Sensor 195 includes substrate 200 having surface 205 formed in a groove profile that is defined by a first sinusoidal component of period p superposed with a second sinusoidal component p/3. In this fashion, sensor 195 exhibits a change in reflectivity at two resonance angles. In other embodiments, surface 205 need not be sinusoidal but may be any groove profile having a first sinusoidal harmonic and a second sinusoidal harmonic. In one embodiment, the amplitude at which the components are superposed is determined in order to ensure that the reflectance anomaly at each resonance angle is of approximately equal magnitude.

As in conventional SPR sensors thin metal layer 210 is formed outwardly from surface 205 of substrate 195 and comprises any suitable metal such as aluminum, gold or silver. Sensitizing layer 230 is selected to interact with a predetermined chemical, biochemical or biological substance 140 contained in sample 150. In one embodiment, sensitizing layer 230 comprises a layer of antigens capable of trapping a complementary antibody. Preferably, sensitizing layer 230 is less than 100 nm thick.

One manner of constructing conventional SPR sensors is to first deposit a layer of photoresist on a substrate. The photoresist is exposed with two interfering laser beams at appropriate angles in order to harden the resist. When the non-exposed photoresist is washed away, the substrate is left within a sinusoidal surface of hardened photoresist. A mold can be made from this photoresist for mass producing grooved substrates from a variety of plastics. The laser beams are interfered with each other according to the equation:

$$d = \frac{\lambda}{\sin\phi_1 - \sin\phi_2}$$

where d equals the period, λ equals the wavelength of the laser beams and $\phi_1$ and $\phi_2$ are the angles of incidence of the two beams. An SPR sensor having a surface profile according to the present invention can be formed by interfering a third beam with the first beam at a third angle of incidence. For example, using a standard argon laser source having a wavelength of 514.4 nm, a first and second laser beam can be interfered at angles of incidence of 60° and 17.1° to form a sinusoidal groove profile having a period of 0.9 μm. Interfering a third laser beam at an angle of incidence of −58.1° with the first laser beam will introduce a harmonic having a period of 0.3 μm, thereby producing a groove profile having a first sinusoidal component of period p superposed with a second sinusoidal component p/3. The amplitude of each sinusoidal component of the groove profile is a function of the intensity of each laser beam exposing the photoresist. Therefore, an SPR sensor that exhibits substantially equal resonance anomalies at each resonance angle can be easily formed.

Figure 4:
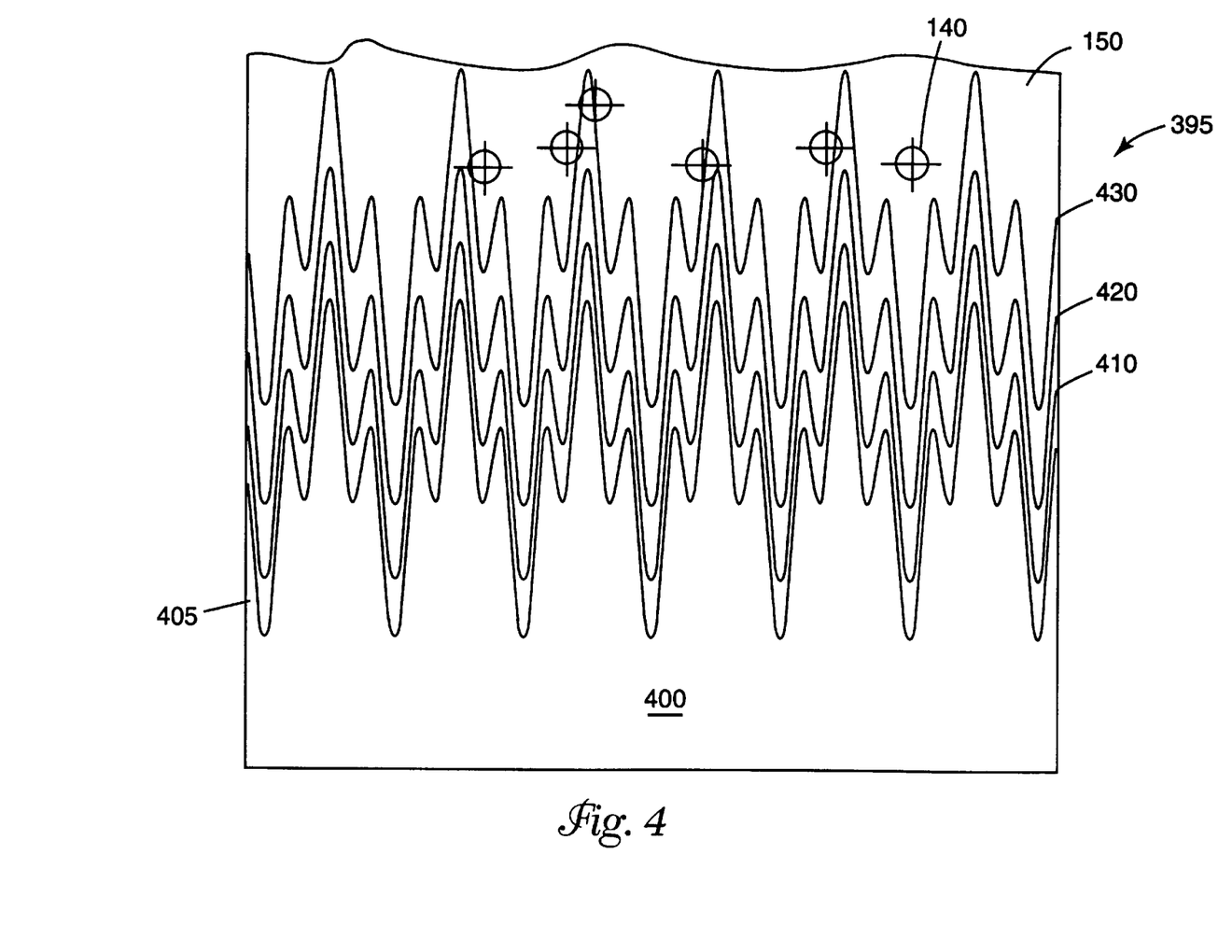
FIG. 4 is a cross-sectional view of one embodiment of a diffraction anomaly sensor having a dielectric-coated metal grating and a groove profile with multiple sinusoidal components.

FIG. 4 illustrates in detail one embodiment of diffraction anomaly sensor 395 having a surface 405 defined by a first sinusoidal component superposed with a second sinusoidal component in accordance with the present invention. Thin metal layer 410 is formed outwardly from surface 405 of substrate 400 and comprises any suitable metal such as aluminum, gold or silver. Dielectric layer 420 is formed outwardly from metal layer 410 and thereby protects metal layer 410 from oxidation and general degradation. In this manner, metal layer 410 may comprise any suitable metal and may be selected to optimize sensitivity. Preferably dielectric layer 420 conforms to the groove profile as illustrated in FIG. 4. The thickness and dielectric constant of dielectric layer 420 directly affect the diffraction anomaly exhibited by sensor 395. Dielectric layer 420 comprises any suitable dielectric material such as silicon nitride, SiN, and is preferably at least 50 nm thick. Alternatively, dielectric layer 420 may have a thickness of at least 100 nm or, more preferably, at least 130 nm.

In one embodiment, sensitizing layer 430 is formed outwardly from dielectric layer 420. Because dielectric layer 420 is disposed between sensitizing layer 430 and metal layer 410, dielectric layer 420 prevents chemical reaction between the metal layer 410 and sensitizing layer 430. Sensitizing layer 430 is selected to interact with a predetermined chemical, biochemical or biological substance 140 contained in sample 150. In this manner, sensitizing layer 430 may comprise a layer of antigens capable of trapping a complementary antibody. In another embodiment, dielectric layer 420 is selected so as to interact directly with substance 140, thereby eliminating the need for sensitizing layer 430.

Unlike conventional SPR sensors, diffraction anomaly sensor 395 exhibits a reflectance dip for light polarized parallel to the grooves of surface 405. When light beam 25 (FIG. 1) strikes sensor 395 at one of the resonance angles, the component of light beam 70 polarized parallel to the grooves is not received by beamsplitter 80 but propagates within dielectric layer 420. In this manner, dielectric layer 420 acts as a waveguide and the controller readily detects the anomaly in reflectivity.

The following equations can be used to select dielectric layer 420 such that a diffraction anomaly angle, $\theta_{SP}$, occurs for component 85 having a polarization parallel to the grooves of surface 405. Using an iterative process, a wavevector for the diffraction anomaly resonance, $k_x$, can be calculated from the following equation:

$$\left(\varepsilon_1\sqrt{\varepsilon_1 k_0^2 - k_x^2} + \varepsilon_0\sqrt{\varepsilon_0 k_0^2 - k_x^2}\right)\left(\varepsilon_2\sqrt{\varepsilon_2 k_0^2 - k_x^2} + \varepsilon_1\sqrt{\varepsilon_1 k_0^2 - k_x^2}\right) +$$
$$\left(\varepsilon_1\sqrt{\varepsilon_1 k_0^2 - k_x^2} - \varepsilon_0\sqrt{\varepsilon_0 k_0^2 - k_x^2}\right)$$
$$\left(\varepsilon_2\sqrt{\varepsilon_2 k_0^2 - k_x^2} - \varepsilon_1\sqrt{\varepsilon_1 k_0^2 - k_x^2}\right)\exp\left(2i\sqrt{\varepsilon_1 k_0^2 - k_x^2}\, d\right) = 0$$

In this equation, $\varepsilon_0$ is the dielectric constant of the medium above the substrate, such as air or water, etc., $\varepsilon_1$ is the dielectric constant of the dielectric layer, and $\varepsilon_2$ is the dielectric constant of the metal film. Furthermore, $k_0$ is a wavevector of the incident light in vacuum and equals $2\pi/\lambda$. Finally, d is the thickness of the dielectric layer.

Once the wavevector for the diffraction anomaly resonance has been found, the following equation can be used to solve for the diffraction anomaly angles, $\theta_{SP}$:

$$\sin\theta_{SP} = -\left(\frac{m\lambda}{n_0 p}\right)\cos\phi_{SP} \pm \sqrt{\left(\frac{k_x}{n_0 k_0}\right)^2 - \left(\frac{m\lambda}{n_0 p}\sin\phi_{SP}\right)^2}.$$

In this equation, $\phi_{SP}$ is the azimuthal angle of incident light beam 25 with respect to the grooves of surface 405, where 0° corresponds to the plane of incidence perpendicular to the groove direction, $n_0$ is the index of refraction of the sample, λ is the wavelength of light beam 25, p is the period of the grooves of surface 405, and m is an integer. Thus, a dielectric layer having a suitable dielectric constant may be readily selected so as to suppress component 85 which has a polarization parallel to the grooves in surface 405 of sensor 395.

Figure 5:
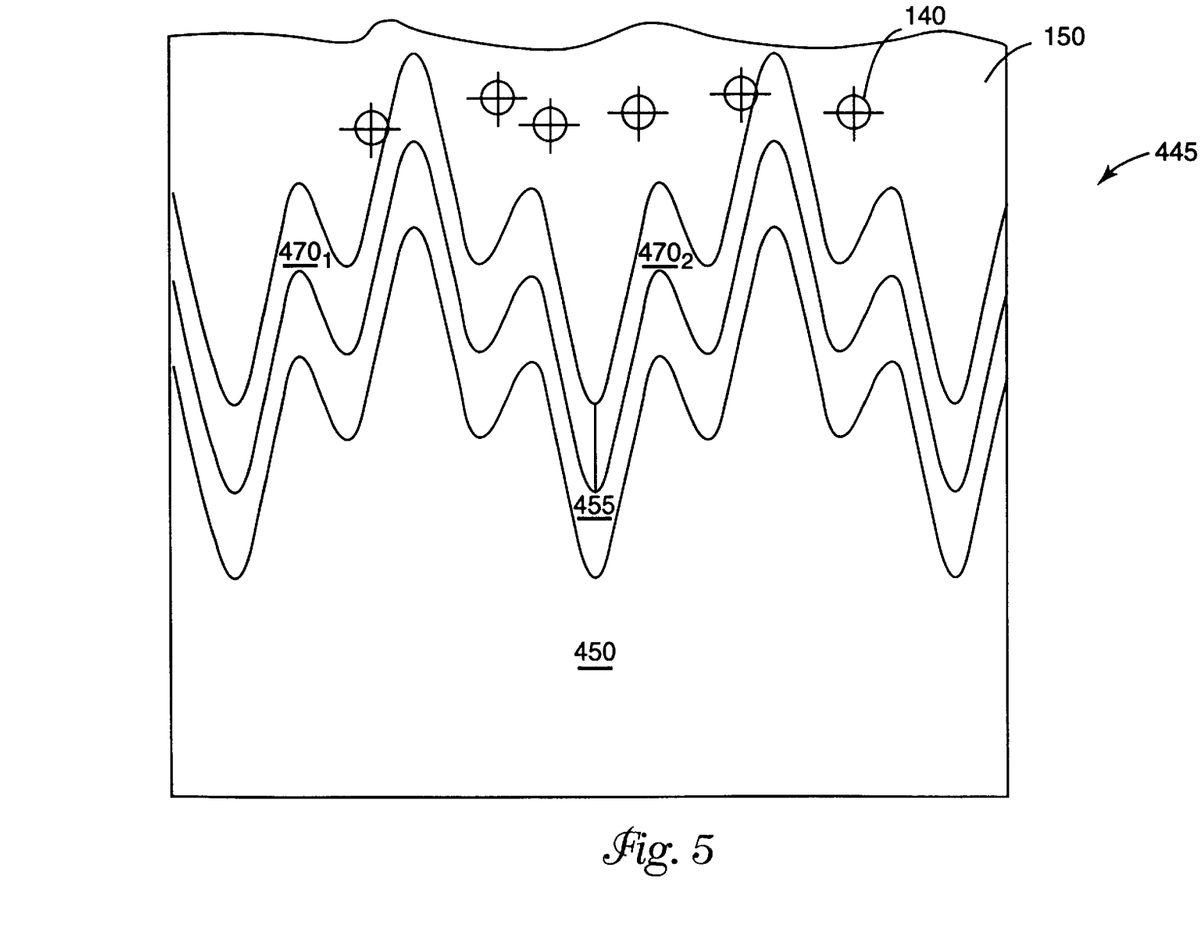
FIG. 5 is a cross-sectional view of one embodiment of a diffraction anomaly sensor having a plurality of dielectric layers sensitized for a variety of targeted substances and a groove profile with multiple sinusoidal components.

FIG. 5 illustrates one embodiment of a diffraction anomaly sensor that is sensitized to interact with a plurality of substances. Sensor 445 includes substrate 450 having a groove profile that is defined by a first sinusoidal component of period p superposed with a second sinusoidal component p/3. In this fashion, sensor 445 exhibits a change in reflectivity at exactly two resonance angles. Thin metal layer 455 is formed outwardly from substrate 450 and is substantially similar to thin metal layer 410 of FIG. 4. A plurality of dielectric layers $470_1$ through $470_N$ are formed along metal layer 210 and are substantially non-overlapping as shown in FIG. 5. Dielectric layers 470 protect metal layer 455 from oxidation and degradation. Each dielectric layer 470 is selected to interact with different chemical, biochemical or biological substance 140 contained in the sample. In this configuration, sensor 445 is sensitized to interact with a variety of substances. One advantage of this configuration is that an operator does not need to reconfigure a sensing system in order to assay different substances. Another advantage is that a single sample may be assayed for a plurality of substances simply by interacting sensor 445 with the sample, selectively exposing dielectric layers 470 with an incident light beam and detecting any change in angular separation of the corresponding diffraction anomaly angles. In one embodiment, dielectric layers 470 have substantially equal thickness of at least 120 nm. In another embodiment, the thickness of dielectric layers 470 varies in order to optimize the sensitivity of sensor 445 to the corresponding substance 140.

Figure 6:
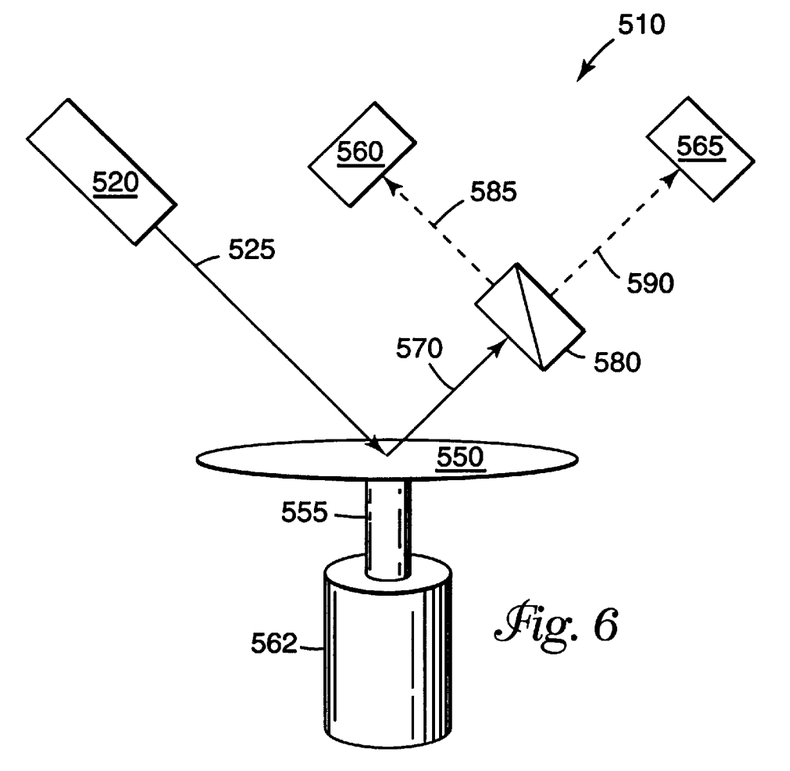
FIG. 6 illustrates one embodiment of a sensing system for assaying a plurality of substances by detecting a change in light received from a rotating sensor disk.

FIG. 6 illustrates another embodiment of a sensing system 510 capable of detecting a plurality of targeted substances using a sensor constructed in accordance with the present invention. Sensing system 510 includes light source 520, sensor disk 550, polarizing beamsplitter 580, detector 560 and detector 565. Light source 520, such as a laser, produces light beam 525 incident upon rotating sensor disk 550. Sensor disk 550 reflects light beam 525 as light beam 570 onto polarizing beamsplitter 580. Polarizing beamsplitter 580 splits light beam 570 into components 585 and 590 which are incident upon detectors 560 and 565, respectively.

In one embodiment, sensor disk 550 is a surface plasmon resonance (SPR) sensor having a metallized diffraction grating. In another embodiment, sensor disk 550 is a diffraction anomaly sensor having a metal grating coated with a dielectric layer. Sensor disk 550 is coupled to shaft 555 such that engagement of motor 560 causes sensor disk 550 to rotate in a circular motion in a plane substantially orthogonal to shaft 555 such that each of a plurality of sensitized regions is sequentially rotated into light beam 525. In one embodiment, a controller (not shown) is coupled to detectors 560 and 565 for calculating a measure of a corresponding targeted substance for each sensing region as a function of a detected change in light 570 reflected by each of the sensitized regions. In this manner, sensing system 510 is capable of easily detecting and measuring the presence of a variety of substances without requiring multiple sensors. The controller may comprise any suitable programmable logic or embedded microprocessor configured to monitor detectors 560 and 565. Furthermore, if complex analysis is required, the controller may employ a neural network or other means for analysis.

In order to assay a sample, sensor disk 550 is typically smeared with the sample and motor 562 is engaged to rotate sensor disk 550. The controller monitors detectors 565 and 560 to determine the presence of any targeted substance in the sample. In another configuration, however, motor 562 is continuously engaged and the controller monitors detector 525 to determine whether a targeted substance is present in a surrounding environment. In either configuration, sensing system 510 can be easily and inexpensively manufactured.

Figure 7:
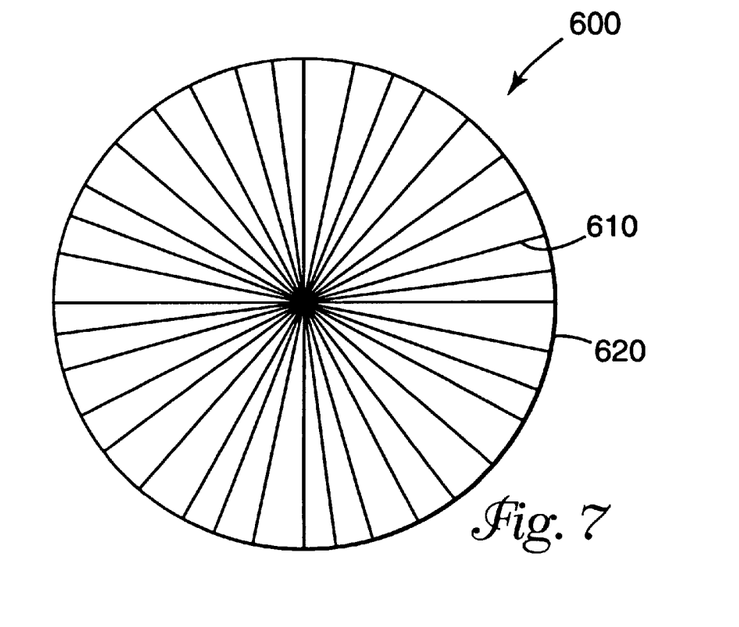
FIG. 7 is a schematic top view of one embodiment of a sensor disk having a plurality of grooves formed according to the present invention and extending radially from a center of the sensor disk.
Figure 8:
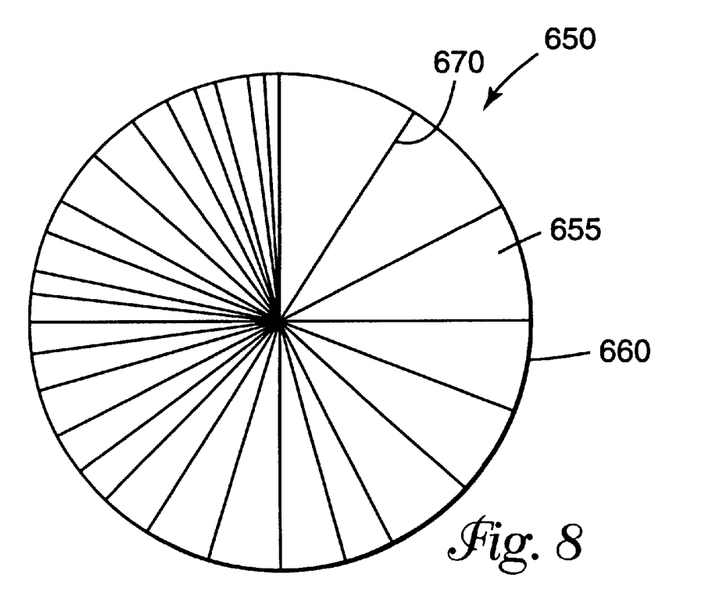
FIG. 8 is a schematic top view of another embodiment of a sensor disk having a plurality of grooves formed according to the present invention and extending radially from a center of the sensor disk.

FIG. 7 is a top view of one embodiment of a sensor disk 600 configured for operation in a sensing system in accordance with the present invention. A diffraction grating is formed on a surface of sensor disk 600 such that grooves 610 extend radially from a center of radial grating sensor disk 600. Grooves 610 follow a profile having multiple sinusoidal harmonics such that sensor disk 600 exhibits a change in reflectivity at multiple resonance angles. Various types of receptive materials are formed on the diffraction grating to form one or more sensitized regions (not shown). The period of grooves 610 increases linearly from the center to an outside edge 620 as measured by the linear distance between adjacent grooves. Therefore, the period of grooves 610 remains constant at a fixed radius around radial grating sensor disk 600. FIG. 8 illustrates a sensor disk 650 having grooves 660 that extend radially yet have a period that varies around the circumference of sensor disk 650. In these configurations, a sensor disk capable of detecting a plurality of targeted substances may be inexpensively manufactured.

Sensor disks 600 (FIG. 7) and 650 (FIG. 8) may be configured as an SPR sensor or as a diffraction anomaly sensor. As SPR sensors, sensor disks 600 and 650 exhibit a change in reflectivity when exposed with light polarized perpendicular to grooves 610. As diffraction anomaly sensors, sensor disks 600 and 650 exhibit a change in reflectivity when exposed with light polarized parallel to grooves 610. Because grooves 610 and 670 are formed in accordance with the present invention, light beam 570 (FIG. 6) exhibits multiple reflective anomalies where the period of the grooves of sensor disk 550 is appropriate for resonance. The new "anomaly positions" for sensor disk 600 are readily determined by translating radiation source 520, and therefore light beam 525, radially across sensor disk 600. However, because the period of grooves 670 of sensor disk 650 vary around the circumference of sensor disk 650, the anomaly positions also shift around the circumference and radiation source 520 need not be translated. The controller calculates a measure of targeted substances based upon relative changes in the respective anomaly positions for each sensitized region of sensor disks 600 and 650. Alternatively, the controller monitors relative changes in anomaly positions for each sensitized region and sounds an alarm when the calculated measure of the corresponding targeted substance exceeds a predetermined threshold.

Figure 9:
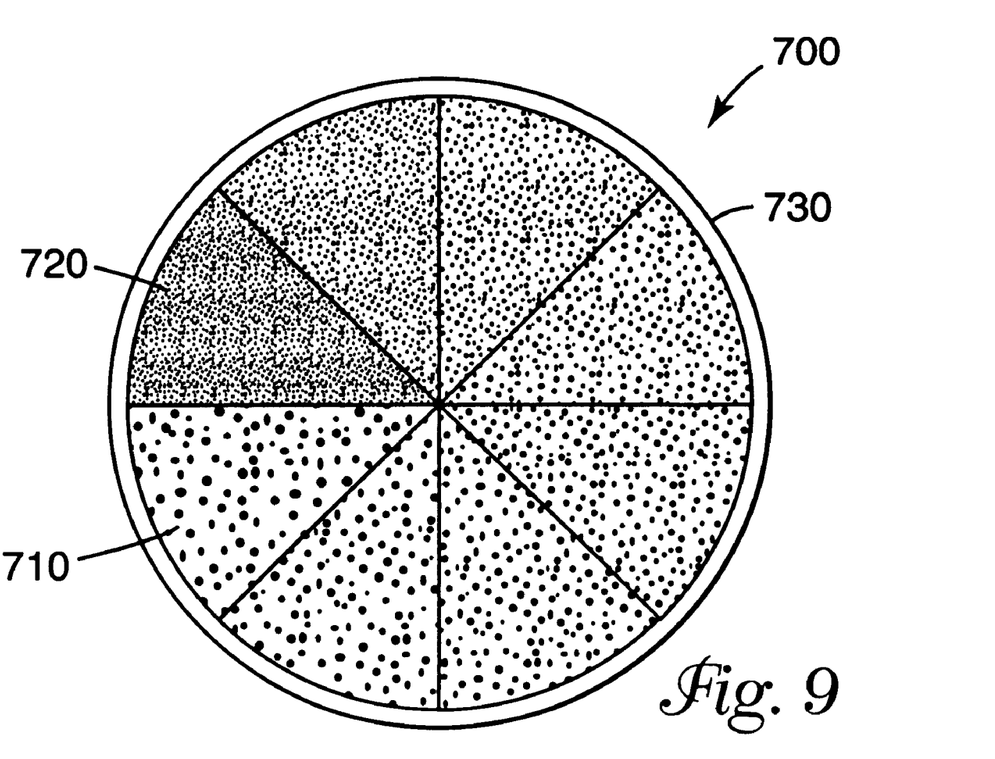
FIG. 9 is a schematic top view of one embodiment of a sensor disk having a metal grating coated with a dielectric layer varying continuously around the circumference of the sensor disk from a minimum thickness to a maximum thickness.

FIG. 9 is a top view of another embodiment of a sensor disk 700 configured for operation in a sensing system in accordance with the present invention. Similar to sensor disks 600 (FIG. 7) and 650 (FIG. 8) described above, constant grating sensor disk 700 may be configured as an SPR sensor or as a diffraction anomaly sensor. Unlike sensor disks 600 and 650, constant grating sensor disk 700 has a diffraction grating formed with grooves having a constant period (not shown). In one embodiment, the grooves of sensor disk 700 are formed in a continuous spiral beginning at a center of sensor disk 700 and spiraling outward until reaching outside edge 730. In another embodiment, the grooves of sensor disk 700 comprise a plurality of concentric grooves. A dielectric layer is formed on the grating of sensor disk 700 having a thickness that continuously increases in a counterclockwise direction such that sensing region 710 has a minimum thickness and sensing region 720 has a maximum thickness. As a diffraction anomaly sensor, it is preferable that the dielectric layer has a minimum thickness of at least 50 nm or, more preferably, at least 130 nm. As an SPR sensor, the dielectric layer must be less than 50 nm thick so as not to suppress the surface plasmon resonance.

When constant grating sensor disk 700 is smeared with a sample, the anomaly positions shift around the circumference of constant grating sensor disk 700. Therefore, the minimum thickness and maximum thickness of the dielectric around the circumference is selected such that changes in reflectivity are readily detectable yet occur within the circumference of constant grating sensor disk 700. Otherwise stated, the thickness of the dielectric layer has a gradient that insures the shift in anomaly positions is readily detectable, but not so large as to shift outside the range of the dielectric thickness.

Several embodiments of an optical assaying method and apparatus have been described. In one aspect, the present invention is an optical sensor having a grooved surface defined by a first sinusoidal component superposed with a second sinusoidal component such that a reflectance anomaly occurs at a first resonance angle and a second resonance angle. As described above, a sensor having multiple resonance angles may be constructed by forming the surface of the sensor to follow a waveform having a plurality of sinusoidal components. Adjusting the amplitude of the sinusoidal components controls the magnitude of the reflective anomaly at each resonance angle. In one embodiment, the constructed sensor is a surface plasmon resonance (SPR) sensor having a metallized diffraction grating that is sensitized for interaction with a targeted substance. In another embodiment, the constructed sensor is a diffraction anomaly sensor having a metal grating that is coated with a dielectric layer. In another aspect, the present invention is a sensing system having a sensor disk having a groove profile so as to exhibit multiple anomalies.

The present invention allows for improved measurement of one or more targeted substances in the sample by monitoring changes in angular distance between resonance angles. This feature increases sensitivity and reduces susceptibility to system drifts due to mechanical motion and thermal changes as compared to conventional diffraction grating sensors.

We claim:

1. A sensor for assaying a substance in a sample comprising:
    a substrate having a grooved surface, wherein a cross-sectional profile of the surface has a first sinusoidal component superposed with a second sinusoidal component, wherein the first sinusoidal component has a first period and the second sinusoidal component has a second period, and further wherein light reflected by the sensor exhibits a resonance anomaly at a first angle of incidence as a function of the first period and at a second angle of incidence as a function of the second period.

2. The sensor of claim 1, wherein the light reflected at the first angle of incidence exhibits a change in reflectivity of at least 20%, and further wherein the light reflected at the second angle of incidence exhibits a change in reflectivity of at least 20%.

3. The sensor of claim 1, further comprising a metal layer formed outwardly from the surface of the substrate and a dielectric layer formed outwardly from the metal layer, the dielectric layer for suppressing reflection of incident light having a polarization parallel to the grooves of the surface.

4. The sensor of claim 3, further comprising a sensitizing layer formed outwardly from the dielectric layer, wherein the sensitizing layer interacts with the substance in the sample.

5. The sensor of claim 3, wherein the dielectric layer has a thickness of at least 5 nm.

6. The sensor of claim 3, wherein the dielectric layer has a thickness of at least 130 nm.

7. The sensor of claim 3, wherein the dielectric layer comprises a plurality of substantially non-overlapping dielectric regions formed along the metal layer.

8. The sensor of claim 7, wherein each dielectric region interacts with at least one of the plurality of substances in the sample.

9. The sensor of claim 4, wherein the sensitizing layer comprises a layer of antigens.

10. The sensor of claim 3, wherein the sensor is a disk and the dielectric layer varies in thickness around a circumference of the sensor disk.

11. The sensor of claim 10, wherein the grooves of the surface are concentric around a center of the sensor disk.

12. The sensor of claim 10, wherein the substrate has a groove spiraling from a center of the sensor disk to an outside edge of the sensor disk.

13. The sensor of claim 1, further comprising a metal layer formed outwardly from the surface of the substrate and a sensitizing layer formed outwardly from the metal layer for interacting with the substance of the sample.

14. The sensor of claim 1, wherein the first and second sinusoidal components are superposed such that a magnitude of light reflected at the first angle of incidence approximately equals a magnitude of light reflected at the second angle of incidence.

15. The sensor of claim 1, wherein the sensor is a disk and the grooves extend radially from a center of the surface.

16. The sensor of claim 15, wherein the grooves have a constant period around a circumference of the disk.

17. The sensor of claim 16, wherein the grooves have a varying period around a circumference of the disk.

18. The method of claim 1, wherein the first sinusoidal component is a first harmonic of the profile and the second sinusoidal component is a third harmonic of the profile.

19. A sensing system, comprising: a sensor having:
    a substrate having a grooved surface, wherein a cross-sectional profile of the surface has a first sinusoidal component superposed with a second sinusoidal component, wherein the first sinusoidal component has a first period and the second sinusoidal component has a second period, and further wherein light reflected by the sensor exhibits a resonance anomaly at a first angle of incidence as a function of the first period and at a second angle of incidence as a function of the second period;
    a light source for exposing the sensor with a light beam;
    a detector receiving light reflected from the sensor and producing an output signal representative of an intensity of the reflected light; and
    a controller coupled to the detector for calculating a measure of the substance in the sample as a function of the output signal.

20. The sensing system of claim 19, wherein the light source exposes the sensor over a range of incidence angles and the controller calculates the measure as a function of a change in angular distance between the first angle of incidence and the second angle of incidence.

21. The sensing system of claim 19, wherein the profile has a third sinusoidal component.

22. The sensing system of claim 19, further comprising a dielectric layer formed outwardly from the metal layer, the dielectric layer for suppressing reflection of incident light having a polarization parallel to the grooves of the substrate.

23. The sensing system of claim 22, further comprising a sensitizing layer formed outwardly from the dielectric layer, wherein the sensitizing layer interacts with the substance in the sample.

24. The sensing system of claim 22, wherein the dielectric layer has a thickness of at least 50 nm.

25. The sensing system of claim 22, wherein the dielectric layer comprises a plurality of substantially non-overlapping dielectric regions formed along the metal layer.

26. The sensing system of claim 25, wherein each dielectric region interacts with at least one of the plurality of substances in the sample.

27. The sensing system of claim 26, further comprising a sensitizing layer formed outwardly from the metal layer for interacting with the substance in the sample.

28. The sensing system of claim 27, wherein the sensitizing layer comprises a layer of antigens.

29. The sensing system of claim 22, wherein the sensor is a rotating disk and the dielectric layer varies in thickness around a circumference of the sensor disk.

30. The sensing system of claim 29, wherein the grooves of the surface are concentric around a center of the disk.

31. The sensing system of claim 29, wherein the substrate has a groove spiraling from a center of the sensor disk to an outside edge of the sensor disk.

32. The sensing system of claim 19, wherein the sensor is a rotating disk and the grooves extend radially from a center of the surface.

33. The sensing system of claim 32, wherein the grooves have a constant period around a circumference of the sensor disk and the light source scans the light radially across the surface of the sensor disk.

34. The sensing system of claim 32, wherein a period of the grooves varies around a circumference of the sensor disk and the light source exposes the sensor disk with the light at a fixed radius from the center of the surface of sensor disk.

35. The sensing system of claim 19, wherein the first sinusoidal component is a first harmonic of the profile and the second sinusoidal component is a third harmonic of the profile.

36. A method for assaying a substance in a sample comprising:
providing a sensor having a substrate with a grooved surface, wherein a cross-sectional profile of the surface has a first sinusoidal component and a second sinusoidal component, wherein the first sinusoidal component has a first period and the second sinusoidal component has a second period, and further wherein light reflected by the sensor exhibits a resonance anomaly at a first angle of incidence as a function of the first period and at a second angle of incidence as a function of the second period;
exposing the sensor with a light beam over a range of incidence angles;
interacting the sensor with the sample; and
determining a measure of the substance in the sample as a function of a change in angular distance between the first and second resonance angles.

37. The method of claim 36, wherein the exposing step comprises polarizing the light beam parallel to the grooves in the metal diffraction grating.

38. The method of claim 36, further comprising sounding an alarm when the determined measure of the substance in the sample exceeds a predetermined threshold.

39. The method of claim 36, wherein the determining step comprises:
splitting a reflected light beam from the sensor into a first light beam having a polarization parallel to grooves in the metal diffraction grating and a second light beam having a polarization perpendicular to grooves of the metal diffraction grating, wherein the first light beam and the second light beam each have a corresponding intensity; and
monitoring a ratio of the intensities of the first light beam and the second light beam.

40. The method of claim 36, wherein the sensor further comprises a dielectric layer formed outwardly from the metal layer, and further wherein the exposing step includes the step of exposing the sensor with a light beam having a component parallel to the grooves of the grating.

41. The method of claim 36, wherein the first sinusoidal component is a first harmonic of the profile and the second sinusoidal component is a third harmonic of the profile.

* * * * *